| United States Patent [19] | [11] Patent Number: 4,797,419 |
| Moos et al. | [45] Date of Patent: Jan. 10, 1989 |

[54] METHOD OF TREATING THE SYMPTOMS OF SENILE COGNITIVE DECLINE EMPLOYING DI- OR TRISUBSTITUTED UREA CHOLINERGIC AGENTS

[75] Inventors: Walter H. Moos; Anthony J. Thomas, both of Ann Arbor, Mich.

[73] Assignee: Warner-Lambert Company, Morris Plains, N.J.

[21] Appl. No.: 926,162

[22] Filed: Nov. 3, 1986

[51] Int. Cl.$^4$ ............................................. A61K 31/17
[52] U.S. Cl. ................................................... 514/588
[58] Field of Search ......................................... 514/588

Primary Examiner—Stanley J. Friedman
Attorney, Agent, or Firm—Ronald A. Daignault

[57] ABSTRACT

Certain trisubstituted alkyl, aryl, pyridinyl, piperidinyl, and piperazinyl urea compounds stimulate the release of acetylcholine and are thus useful agents for the treatment of senile cognitive decline characterized by decreased cerebral acetylcholine production or release.

A method for treating the symptoms of senile cognitive decline is disclosed.

14 Claims, No Drawings

METHOD OF TREATING THE SYMPTOMS OF SENILE COGNITIVE DECLINE EMPLOYING DI- OR TRISUBSTITUTED UREA CHOLINERGIC AGENTS

BACKGROUND OF THE INVENTION

The present invention relates to a pharmaceutical methods of treatment. More particularly, this invention is concerned with a pharmaceutical method of treating the symptoms of senile cognitive decline characterized by the decreased production or release of acetylcholine.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced by as much as ninety percent. (See Davies, et al, *The Lancet*, 1976 (Vol. 2): 1403; Perry, et al, *J. Neurol. Sci.* 34: 247-265 (1977); and White et al., *The Lancet*, 1977 (Volume 1): 668-670).

Since CAT catalyzes the synthesis of acetylcholine from its precursors choline and acetyl coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory formation.

The cholinergic hypothesis suggests that drugs which restore acetylcholine levels or which mimic the action of acetylcholine (i.e., are cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction. (See C. Peterson and G. E. Gibson, *Neurobiol. Aging*, 4: 25-30 (1983). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine. (See H. P. Davis, et al, *Exp. Aging Res.*, 9: 211-214 (1983)).

It has been known for some time that the natural alkaloid, muscarine, has the ability to act relatively selectively at autonomic effector cells to produce qualitatively the same effects as acetylcholine. Two related alkaloids, pilocarpine and arecoline, have the same principal sites of action as muscarine and acetylcholine and are thus classified as having "muscarinic" action. Although these naturally occurring alkaloids are of great value as pharmacological tools, present clinical use is largely restricted to the use of pilocarpine as a miotic agent.

Arecoline (the methyl ester of 1,2,5,6-tetrahydro-1-methyl-3-pyridinecarboxylic acid) is the chief alkaloid found in betel nuts (*Areca catechu*). Betel nuts have been chewed by natives of the East Indies since early times as a euphoretic. The present pharmaceutical utility of arecoline, however, has been limited to its use as a veterinary anthelmintic agent.

Recently it has been demonstrated that arecoline is effective in ameliorating some of the symptoms of cognitive disorders in patients clinically diagnosed as having presenile primary degenerative dementia. Significant improvement was observed in a test of picture recognition after administration of arecoline to patients in a double blind study. (See Christie, et al, *Brit. J. Psychiatry*, 138: 46-50 (1981)).

SUMMARY OF THE INVENTION

The present invention provides a method of treating the symptoms of senile cognitive decline characterized by decreased cerebral production or release of acetylcholine comprising administering to a patient in need of such treatment an acetylcholine-releasing effective amount of a compound as described below.

The compounds of the present invention having analgesic or cholinergic properties have the formula

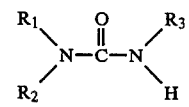

wherein $R_1$, $R_2$ and $R_3$ are each independently hydrogen; straight or branched alkyl of from one to twenty carbon atoms; straight or branched alkenyl of from two to twenty carbon atoms; straight or branched alkynyl of from two to twenty carbon atoms; cycloalkyl of from three to eight carbon atoms; phenyl; phenyl substituted with alkyl of from one to four carbon atoms, alkyloxy of from one to four carbon atoms, chlorine, bromine, hydroxyl, nitro, —$SO_3H$, —$SO_3$-alkyl (wherein alkyl is from one to four carbon atoms), or —$SO_2NR_4R_5$ (wherein $R_4$ and $R_5$ are independently hydrogen or alkyl of from one to four carbon atoms), trifluoromethyl, or $NR_4R_5$ where $R_4$ and $R_5$ are as defined above; with the proviso that only one of $R_1$, $R_2$, or $R_3$ may be hydrogen.

Alternatively, $R_1$ and $R_2$ may, when taken together with the nitrogen atom to which they are attached, form a ring denoted by

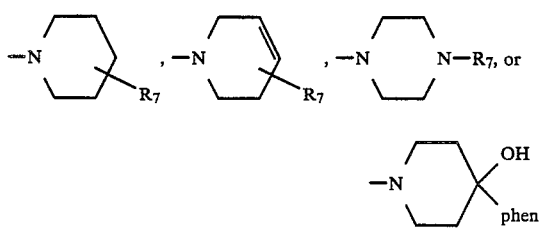

where $R_7$ is hydrogen; alkyl of from one to four carbon atoms; phenyl; 2-, 3-, or 4-pyridinyl; phenylalkyl of from seven to nine carbon atoms; or phenyl substituted with alkyl of from one to four carbon atoms, alkyloxy of from one to four carbon atoms, halogen, hydroxyl, nitro, —$SO_3H$, —$SO_3$-alkyl (wherein alkyl is from one to four Carbon atoms), or —$SO_2NR_4R_5$ (wherein $R_4$ and $R_5$ are independently hydrogen or alkyl of from one to four carbon atoms), trifluoromethyl, or $NR_4R_5$ where $R_4$ and $R_5$ are as defined above.

The present invention also includes pharmaceutically acceptable salts of the above-described compounds.

DETAILED DESCRIPTION

The compounds employed in the method of the present invention form a class of disubstituted or trisubstituted derivatives of urea which possess cholinergic or cholino- mimetic activity and thus are useful in the treatment of senile cognitive decline characterized by decreased cerebral acetylcholine production or release.

These compounds constitute a class of disubstituted or trisubstituted ureas. In the case of disubstituted urea compounds of the present invention, the two substituent groups may both reside on one nitrogen of the urea moiety, or one substituent group on each of the nitrogen atoms of the urea moiety.

Substituent groups are independently selected from alkyl of from one to twenty carbon atoms; straight or branched alkenyl of from two to twenty carbon atoms; straight or branched alkynyl of from two to twenty carbon atoms; or cycloalkyl of from three to eight carbon atom; phenyl; phenyl substituted with alkyl of from one to four carbon atoms, alkyloxy of from one to four carbon atoms, chlorine, bromine, hydroxyl, nitro, —$SO_3H$, —$SO_3$-alkyl (wherein alkyl is from one to four carbon atoms), or —$SO_2NR_4R_5$ (wherein $R_4$ and $R_5$ are independently hydrogen or alkyl of from one to four carbon atoms), trifluoromethyl, or $NR_4R_5$ where $R_4$ and $R_5$ are as defined above.

Alternatively, the nitrogen may form, together with its substituent groups, a ring denoted by

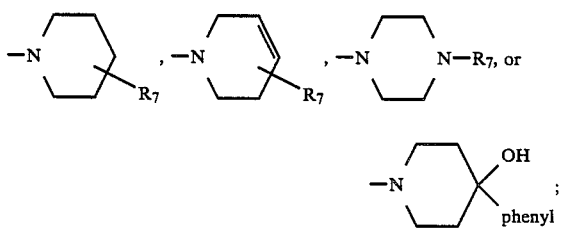

where $R_7$ is hydrogen; alkyl of from one to four carbon atoms; phenyl; 2-, 3-, or 4-pyridinyl; phenylalkyl of from seven to nine carbon atoms; or phenyl substituted with alkyl of from one to four carbon atoms, alkyloxy of from one to four carbon atoms, halogen, hydroxyl, nitro, —$SO_3H$, —$SO_3$-alkyl (wherein alkyl is from one to four carbon atoms), or —$SO_2NR_4R_5$ (wherein $R_4$ and $R_5$ are independently hydrogen or alkyl of from one to four carbon atoms), trifluoromethyl, or $NR_4R_5$ where $R_4$ and $R_5$ are as defined above.

As used throughout this specification and the appended claims, the term "alkyl" denotes a straight or branched hydrocarbon group derived from an alkane by the removal of a single hydrogen atom as, for example, methyl, ethyl, propyl, pentyl, octyl, decyl, dodecyl, hexadecyl, and eicosyl. Branched alkyl groups are exemplified by such groups as isopropyl, n-, sec-, iso-, and tert-butyl, and the like.

The term "alkenyl" denotes a straight or branched hydrocarbon group derived from an alkene by the removal of a single hydrogen atom as, for example, ethenyl, propenyl, butenyl, octenyl, dodecenyl, eicosenyl, and the like.

Similarly, the term "alkynyl" denotes a straight or branched hydrocarbon group derived from an alkyne by the removal of a single hydrogen atom.

"Cycloalkyl of from three to eight carbon atoms" includes cyclopropyl, cyclobutyl, cyclopentyl, cyclohexyl, and cycloheptyl, cyclooctyl, as well as alkylated cycloalkyl groups such as methylcyclopentyl, methyl- and ethylcyclohexyl, and the like.

In another sub-generic aspect of the present invention, the groups $R_1$ and $R_2$ may join together with the nitrogen atom to which they are attached to form a piperazinyl ring which is substituted at the opposite ring-nitrogen atom with alkyl; phenyl; 2-, 3-, or 4-pyridinyl; phenylalkyl; or phenyl substituted with alkyl, alkyloxy, halogen, hydroxyl, nitro, —$SO_3H$, —$SO_3$-alkyl (wherein alkyl is from one to four carbon atoms), or —$SO_2NR_4R_5$ (wherein $R_4$ and $R_5$ are independently hydrogen or alkyl of from one to four carbon atoms), trifluoromethyl, or $NR_4R_5$ where $R_4$ and $R_5$ are as defined above.

As used throughout this specification and the appended claims, "alkyloxy" denotes an alkyl group, as defined above, attached to the parent molecular moiety through an oxygen atom.

The term "phenylalkyl" denotes a benzene ring, attached through a branched or unbranched alkyl group to the parent molecular moiety.

In another sub-generic aspect of the invention, the groups $R_1$ and $R_2$ may join together with the nitrogen atom to which they are attached to form a piperidinyl or 3,6-dihydro-1(2H)-pyridinyl ring, simliarly substituted with alkyl; phenyl; 2-, 3-, or 4-pyridinyl; phenylalkyl; or phenyl substituted with alkyl, alkyloxy, halogen, hydroxyl, nitro, —$SO_3H$, —$SO_3$-alkyl (wherein alkyl is from one to four carbon atoms), or —$SO_2NR_4 R_5$ (wherein $R_4$ and $R_5$ are independently hydrogen or alkyl of from one to four carbon atoms), trifluoromethyl, or $NR_4R_5$ where $R_4$ and $R_5$ are as defined above.

Compounds contemplated as falling within the scope of the method of the present invention are exemplified, but not limited to the following:

N'-Butyl-N,N-dicyclohexylurea.
N'-Methyl-N,N-diphenylurea.
N'-Ethyl-N,N-diphenylurea.
N'-Isopropyl-N,N-diphenylurea.
N'-Cyclopentyl-N,N-diphenylurea.
N,N,N'-Triphenylurea.
N'-(3,4-Dichlorophenyl)-N,N-diphenylurea.

N'-(5-Chloro-2-methoxyphenyl)-N,N-dicyclohexylurea.

N,N-Diphenyl-N'-(4-pyridinyl)urea.

N,N-Dicyclohexyl-N'-[3-chloro-2-(trifluoromethyl)phenyl]urea.

N-Cyclohexyl-N-methyl-N'-octadecylurea.

N-(2,4-Difluorophenyl)-2,6-dimethyl-1-piperidine carboxamide.

N-(3-Chloro-2-methylphenyl)-4-methyl-1-piperidine carboxamide.

N,N'-Diphenylurea.

N,N-Diphenylurea.

The compounds of the present invention may be prepared by either of the two methods detailed below in Reaction Scheme 1 or Reaction Scheme 2.

In the method detailed in Reaction Scheme 1, the disubstituted amine compounds, 1 where $R_1$ and $R_2$ are as defined above, are generally known compounds or, if not previously known, are synthesized by methods well known in the art. (See, for example, M. P. Sammes, et al, *J. Chem. Soc. Perkin Trans.* 1, (5), 973–978 (1983) and earlier references cited therein.)

Compound 1 is converted to the corresponding disubstituted carbamic chloride, 2, by reaction with phosgene in an inert hydrocarbon solvent such as, for example, benzene, or toluene. The carbamic chloride compound, 2, is then reacted with the the desired amine compound 3, where $R_3$ is as defined above, to produce the desired trisubstituted urea compounds, 4. This reaction is generally carried out in an inert solvent such as chloroform in the presence of an acid scavenger such as triethylamine. The carbamic chloride compound is slowly added to the diamine and, after addition is complete, the mixture is heated under reflux for a period of from twenty-four to seventy-two hours. The desired product is then separated from the reaction mixture and purified by conventional methods.

Alternatively, the compounds of the method of this invention may be prepared by the method detailed in Reaction Scheme 2. In that method, the disubstituted amine compounds, 1, are reacted with the desired isocyaates, 5, using standard methodology. For example, an isocyanate, 5, is reacted with the desired amine compound, 3, to produce the desired trisubstituted (urea compound, 4. This reaction is generally carried out in an inert solvent such as an ether. The amine is slowly added to the isocyanate and Reaction Scheme 1

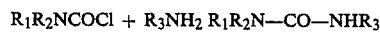

$$R_1R_2NH + COCl_2 \rightarrow R_1R_2NCOCl$$
$$1 \qquad\qquad 2$$

$$R_1R_2NCOCl + R_3NH_2 \rightarrow R_1R_2N-CO-NHR_3$$
$$2 \qquad\qquad 3 \qquad\qquad 4$$

Reaction Scheme 2

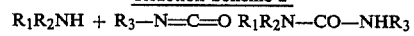

$$R_1R_2NH + R_3-N=C=O \rightarrow R_1R_2N-CO-NHR_3$$
$$1 \qquad\qquad 5 \qquad\qquad 4$$

allowed to react with stirring at room temperature for a period of about 2–48 hours. The product is then separated and purified by conventional means.

Compounds of the present invention where the $R_1$, $R_2$, or $R_3$ groups contain a basic nitrogen atom are capable of forming acid addition salts with pharmaceutically acceptable acids.

Examples of suitable acids for the formation of pharmaceutically acceptable salts of compounds of this invention are hydrochloric, sulfuric, phosphoric, acetic, benzoic, citric, malonic, salicylic, malic, fumaric, succinic, tartaric, lactic, gluconic, ascorbic, maleic, benzenesulfonic, methane- and ethanesulfonic, hydroxymethanesulfonic and hydroxyethanesulfonic, aspartic, and the like.

The salts are prepared by contacting the free base form of the compounds of this invention with a sufficient amount of the desired acid to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate may be utilized for this purpose.

The compounds of this invention act by stimulating the release of acetylcholine or, in some cases, by mimicking the action of cholinergic agents and are thus useful as agents for the treatment of cognitive dysfunctions which arise as a result of decreased cerebral acetylcholine production or release such as in the case of cognitive decline in the elderly.

The cholinergic activity of the compounds of the present invention was evaluated by determining the percent increase in spontaneous release or percent increase in potassium ion stimulated release of acetylcholine in the hippocampus of standard laboratory rats.

For the cholinergic system it has been shown that $^3H$-choline can be actively taken into the brain tissue by a sodium dependent high affinity choline uptake (HACU) system at concentrations lower than that of of the HACU system and combine with acetyl CoA due to the action of choline acetyltransferase (CAT) to form $^3H$-ACh This can then be released under depolarizing conditions (e.g. by the action of potassium ion) in the presence of $Ca^{-2}$.

Several representative compounds of the present invention were tested by this screening method, and the results appear in Table 1.

In Table 2, the data are presented for several representative compounds of this invention in the scopolamine-induced spontaneous swim activity.

Swimming activity of standard laboratory rats following the administration of the anticholinergic agent, scopolamine, has been found to be a rapid and reliable behavioral screen for compounds with cholinergic activity. The procedures for this test are basically a variation of those used to measure open field activity except that the animals must swim rather than run.

Untreated rats in this test will swim between 20 and 30 meters during a five minute test period. Rats given scopolamine at doses of 0.1 mg/kg develop a stereotypical swimming hyperactivity. Typically, the swimming distance increases 75–125% above baseline levels. This increase in activity associated with the administration of scopolomine is reversed by the administration of either the anticholin- esterase, physostigmine, or a compound of the present invention.

The effect of scopolamine on swimming behavior has been determined to be centrally mediated since (1) the quaternary amine of scopolamine (scopolamine methyl nitrate) does not produce any behavioral change in this test and (2) the quaternary amine of physostigmine (neostigmine) does not reverse the effect of scopolamine.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation in is unit dosage form. In such form, the preparation is divided into unit doses containing appropriate quantities of the active component. The unit dosage form can be a packaged preparation, the package containing discrete quantities of the preparation, for example, packeted tablets, capsules, and powers in vials or ampoules. The unit dosage form can also be a capsule, cachet, or tablet itself, or it can be the appropriate number of any of these packaged forms.

In therapeutic use as agents for treating the symptoms of senile cognitive decline, the compounds utilized in the pharmaceutical method of this invention are administered to the patient at dosage levels of from 0.7 to 7000 mg per day. For a normal human adult of approximately 70 kg of body weight, this translates into a dosage of from 0.01 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

TABLE 1

$$\begin{array}{c} R_1 \\ \phantom{N} \diagdown \phantom{C} \phantom{O} \phantom{C} \diagup \phantom{N} R_3 \\ N-C-N \\ \diagup \phantom{NNN} \diagdown \\ R_2 \phantom{NNNNN} H \end{array}$$

| | | | Percent Increase Acetylcholine Release | |
|---|---|---|---|---|
| | | | Spontaneous | K+ Stimulated |
| $R_1$ | $R_2$ | $R_3$ | (Molar conc. given in parentheses) | |
| Cyclohexyl | Cyclohexyl | n-Butyl | −9.40 | 98.20 |
| Cyclohexyl | Cyclohexyl | 3-Chloro-2-trifluoromethylphenyl | −13.7 | 72.40 |
| Phenyl | Phenyl | Phenyl | −22 | 83.80 |
| 4-Methylpiperidinyl | | 3-Chloro-2-methylphenyl | −13.1 | 23.25 |
| 2,6-Dimethylpiperidin-1-yl | | 2,4-Difluorophenyl | 2.70 | 35.93 |
| Phenyl | Phenyl | Hydrogen | −7.8 | 35.8 |
| Phenyl | Hydrogen | Phenyl | −11.0 | 60.7 |

TABLE 2

$$\begin{array}{c} R_1 \\ \phantom{N} \diagdown \phantom{C} \phantom{O} \phantom{C} \diagup \phantom{N} R_3 \\ N-C-N \\ \diagup \phantom{NNN} \diagdown \\ R_2 \phantom{NNNNN} H \end{array}$$

| | | | Percent Reversal of Scopolamine-Induced Swimming Activity at Various Doses (mg/kg) | | | | |
|---|---|---|---|---|---|---|---|
| $R_1$ | $R_2$ | $R_3$ | 0.32 | 1.0 | 3.2 | 1.0 | 32 |
| Phenyl | Phenyl | 3,4-Dichlorophenyl | N | | N | | C |

A = Active - Reversal equal to control levels
C = Marginally active - Reversal not significantly different from control or scopolamine levels
N = Inactive - Reversal equal to scopolamine levels A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

The following preparative examples are provided to enable one skilled in the art to practice the invention. They are illustrative of the methods employed to prepare the compounds listed in Table 3 and are not to be read as limiting the scope of the invention as it is defined by the appended claims.

EXAMPLE 1

Preparation of triphenylurea

Diphenylcarbamic chloride (23 g, 0.1 mol, Aldrich Chemical Co., Milwaukee, Wis., U.S.A.) was added to a solution of 10.1 g of triethylamine and 9.3 g (0.1 mol) of benzeneamine in 150 ml of chloroform. The resulting solution was heated under reflux overnight. The solution was cooled to room temperature and washed three times with 100-ml portions of brine solution, dried over anhydrous magnesium sulfate, and evaporated to give an off-white solid which was triturated with diethyl ether to give triphenylurea as a white solid, mp 136°–138° C.

EXAMPLE 2

Preparation of N,N-diphenyl-N'-(4-pyridinyl)urea

Employing the general method of Example 1, 27.5 g (0.12 mol) of diphenylcarbamic chloride and 20 g (0.12 mol) of 4-aminopyridine were heated under reflux for two hours in 150 ml of chloroform containing 12.0 g (0.12 mol) of triethylamine to produce the title compound as a pale yellow solid.

The crude product was chromatographed on a silida gel column, eluting with 10% 2-propanol in chloroform to produce pure product as a white solid.

EXAMPLE 3

Preparation of N,N-diphenyl-N'-(3,4-dichlorophenyl)urea 3,4-Dichloroaniline (5.35 g, 0.033 mol) was dissolved in 100 ml of chloroform and 7.65 g (0.033 mol) of diphenylcarbamic chloride and 3.33 g (0.033 mol) of triethylamine were added.

The resulting mixture was heated under reflux for two and one-half hours, cooled to room temperature, washed three times with 150-ml portions of brine solution and dried. Evaporation of the solvent yielded an off-white solid which, after washing with diethyl ether and drying overnight yielded the title compound as a white solid, mp 139°–142° C.

Using the general methods outlined above the following compounds are prepared:

TABLE 3

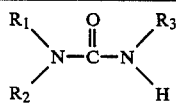

| $R_1$ | $R_2$ | $R_3$ | M.p. |
|---|---|---|---|
| Phenyl | Phenyl | Methyl | 171–174° C. |

TABLE 3-continued

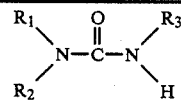

| $R_1$ | $R_2$ | $R_3$ | M.p. |
|---|---|---|---|
| Phenyl | Phenyl | Ethyl | 76–79° C. |
| Phenyl | Phenyl | Isopropyl | 105–108° C. |
| Phenyl | Phenyl | Cyclopentyl | 136–138° C. |

We claim:

1. A method of alleviating cholinergic deficits that accompany aging or dementia comprising administering to a patient suffering therefrom an effective amount of a compound having the formula

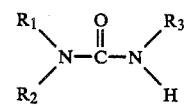

wherein $R_1$, $R_2$ and $R_3$ are each independently hydrogen; straight or branched alkyl of from one to twenty carbon atoms; straight or branhed alkenyl of from two to twenty carbon atoms; straight or branched alkynyl of from two to twenty carbon atoms; cycloalkyl of from three to eight carbon atoms; phenyl; phenyl substituted with alkyl of from one to four carbon atoms, alkyloxy of from one to four carbon atoms, chlorine, bromine, hydroxyl, nitro, —$SO_3H$, —$SO_3$-alkyl (wherein alkyl is from one to four carbon atoms), independently hydrogen or alkyl of from one to four carbon atoms, trifluoromethyl, or $NR_4R_5$ where $R_4$ and $R_5$ are independently hydrogen or alkyl of from one to four carbon atoms or trifluoromethyl; with the proviso that only one of $R_1$, $R_2$ or $R_3$ may be hydrogen at any time.

2. A method as defined by claim 1 wherein said compound is N'-butyl-N,N-dicyclohexylurea.

3. A method as defined by claim 1 wherein said compound is N'-methyl-N,N-diphenylurea.

4. A method as defined by claim 1 wherein said compound is N'-ethyl-N,N-diphenylurea.

5. A method as defined by claim 1 wherein said compound is N'-isopropyl-N,N-diphenylurea.

6. A method as defined by claim 1 wherein said compound is N'-cyclopentyl-N,N-diphenylurea.

7. A method as defined by claim 1 wherein said compound is N,N,N'-triphenylurea.

8. A method as defined by claim 1 wherein said compound is N'-(3,4-dichlorophenyl)-N,N-diphenylurea.

9. A method as defined by claim 1 wherein said compound is N'-(5-chloro-2-methoxyphenyl)-N,N-dicyclohexylurea.

10. A method as defined by claim 1 wherein said compound is N-cyclohexyl-N-methyl-N'-octadecylurea.

11. A method as defined by claim 1 wherein said compound is N'-[3-chloro-2-(trifluoromethyl)phenyl]urea.

12. A method as defined by claim 1 wherein said compound is N,N-diphenyl-N'-(4-pyridinylurea).

13. A method as defined by claim 1 wherein said compound is N,N-diphenylurea.

14. A method as defined by claim 1 wherein said compound is N,N'-diphenylurea.

* * * * *